United States Patent [19]

Ohnaka et al.

[11] Patent Number: 5,045,067
[45] Date of Patent: Sep. 3, 1991

[54] BREAKAWAY TUBE ASSEMBLY

[75] Inventors: Yukihiro Ohnaka, Tokyo; Yoshikazu Kiso, Fujinomiya, both of Japan

[73] Assignee: Terumo Kabushiki Kaisha, Tokyo, Japan

[21] Appl. No.: 415,341
[22] PCT Filed: Mar. 18, 1988
[86] PCT No.: PCT/JP88/00285
   § 371 Date: Sep. 11, 1989
   § 102(e) Date: Sep. 11, 1989
[87] PCT Pub. No.: WO88/06902
   PCT Pub. Date: Sep. 22, 1988

[30] Foreign Application Priority Data

Mar. 19, 1987 [JP] Japan .................... 62-64864

[51] Int. Cl.$^5$ ............................ A61M 5/00
[52] U.S. Cl. .................... 604/244; 604/256; 604/905; 215/32; 220/265
[58] Field of Search ............ 604/244, 256, 280, 283, 604/284, 905, 246, 148; 220/265, 276; 215/32, 253, 254

[56] References Cited

U.S. PATENT DOCUMENTS

| 943,231 | 12/1909 | Adelson | 215/32 |
| 1,127,687 | 2/1915 | Slattengren | 215/32 |
| 3,749,271 | 7/1973 | Ellis, Jr. et al. | 215/32 |
| 4,294,247 | 10/1981 | Carter et al. | 604/244 X |
| 4,340,049 | 7/1982 | Munsch | 604/244 X |
| 4,655,764 | 4/1987 | Sato | 604/905 X |
| 4,731,001 | 3/1988 | Matkovich | 604/263 |
| 4,862,226 | 8/1989 | Imaizumi et al. | 215/32 X |
| 4,899,903 | 2/1990 | Miyasaka et al. | 220/266 |
| 4,911,696 | 3/1990 | Miyasaka et al. | 604/244 |
| 4,915,704 | 4/1990 | Miyasaka et al. | 604/256 |

FOREIGN PATENT DOCUMENTS

| 2549097 | 5/1977 | Fed. Rep. of Germany | 604/905 |
| 1280708 | 11/1961 | France . | |
| 635245 | 3/1983 | Switzerland . | |
| 823481 | 11/1959 | United Kingdom . | |

OTHER PUBLICATIONS

Japanese Kukai 56-60566, May 25, 1981.

Primary Examiner—John D. Yasko
Assistant Examiner—Adam J. Cermak
Attorney, Agent, or Firm—Frishauf, Holtz, Goodman & Woodward

[57] ABSTRACT

A tube assembly is provided which includes a tubular body of rigid resin having an open end and provided with a substantially annular frangible portion and a plug of flexible resin mounted in sealing fit on the tubular body for closing the open end.

6 Claims, 4 Drawing Sheets

PRIOR ART

BREAKAWAY TUBE ASSEMBLY

BACKGROUND OF THE INVENTION

1. Field of the Invention

This invention relates to a tube assembly with a breakaway plug means. More particularly, it relates to a tube assembly having a breakaway plug means which is unlikely to be ruptured or contaminated before use, but readily broken away on use.

2. Discussion of Prior Art

In some branch tubes such as four-way branch tubes for use in combination with blood collection bags, all the branches are not used at the same time, but they are used one by one in successive steps. To prevent the flow path from being contaminated from a branch which is not in use, the branch not in use should be completely sealed with a plug or a suitable closure. Upon use of the branch which has been sealed with the plug, it is necessary that the plug be readily broken and removed to open the associated branch to allow for connection to another member such as a tube having a puncture needle.

Known in the art is a four-way branch tube with a click cap. The click cap is used as the plug that covers the opening of a branch of the branch tube. The branch can be opened simply by breaking or tearing off the click cap.

One example of the prior art click caps is illustrated in FIG. 5. A tubular body 1' has an open end 4'. A plug 2' having a frangible portion 15' is mounted on and secured to the open end portion. The plug 2' is covered with a protector 40 if desired. On use, the protector 40 or the plug 2' is manually grasped and twisted to break away or twist off the plug 2' at the frangible portion 15'. Then the tubular body 1' is ready for connection with another tubular member.

The plug is generally secured to the tubular body by a blocking bond by utilizing the heat available during autoclave sterilization, and not by an adhesive bond. To this end, the plug is formed of relatively flexible material liable to blocking such as polyvinyl chloride (PVC). The prior art tube assembly has the likelihood that it can be fractured when an external stress is accidentally applied during manufacturing or transportation or even contaminated at the fractured portion. This is particularly true when the plug is not covered with the protector. The plug formed of relatively flexible material has another problem when it is desired to twist off the plug. Click fracture of the plug is difficult because the plug as a whole is softly deformed.

Even when the plug 2' is covered with the protector 40 of rigid resin such as polypropylene to prevent accidental rupture by an external stress as shown in FIG. 5, the problem that the plug 2' itself is deformed to prevent click rupture remains unsolved. Since the plug 2' and the protector 40 are separately molded and then engaged, the use of the protector adds to the manufacturing process and makes the process complicated, increasing the cost.

SUMMARY OF THE INVENTION

An object of the present invention is to provide a tube assembly having a breakaway plug structure which is not likely to be accidentally ruptured or contaminated during manufacture or transportation, but can be readily torn off upon use.

According to the present invention, there is provided a tube assembly comprising a tubular body of rigid resin having an open end, and a plug means of flexible resin mounted in sealing fit on the tubular body for closing the open end. The tubular body is provided with a substantially annular frangible portion at a predetermined position in proximity to the open end.

In one preferred embodiment, the tubular body includes an extension having a reduced outer diameter over which the plug means is fitted.

The plug means is preferably in blocking bond to the tubular body.

BRIEF DESCRIPTION OF THE DRAWINGS

The above and other objects, features, and advantages of the invention will be better understood by reading the following description taken in conjunction with the accompanying drawings, in which.

DESCRIPTION OF THE PREFERRED EMBODIMENT

The tube assembly of the present invention includes a tubular body having an open end. Any tubular body having opposed open ends between which a flow path extends may be employed. Although a commonly used four-way branch tube is referred to as a typical example in the following description, the present invention is not limited to the four-way branch tube.

Figure 1:
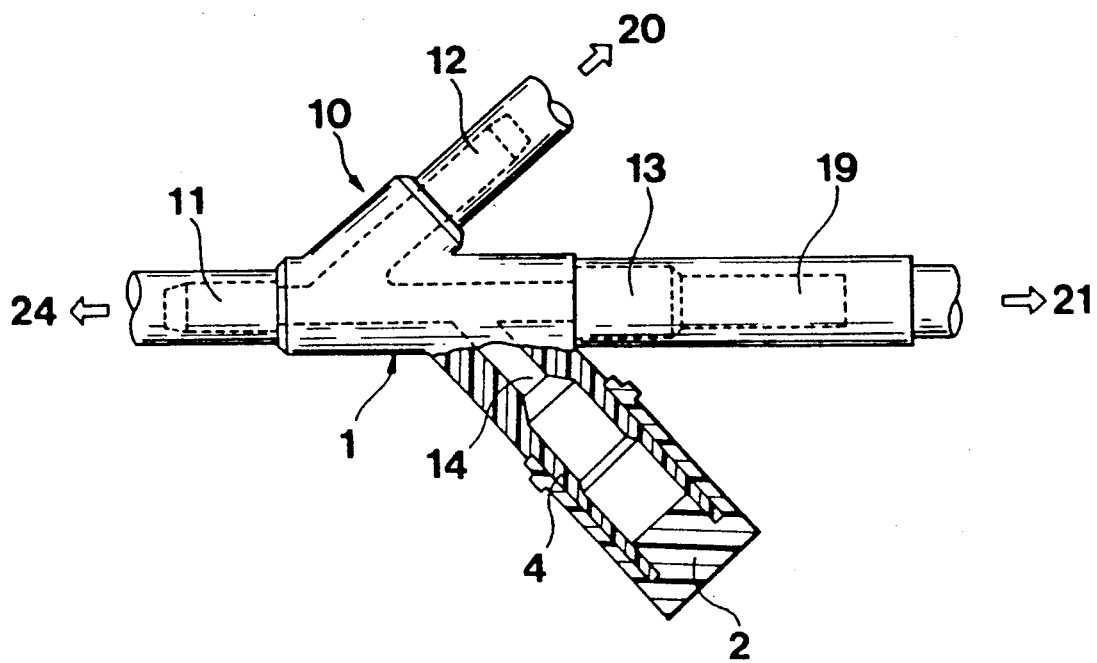
FIG. 1 is a partially cross-sectional plane view of a tube assembly with a breakaway plug structure according to one embodiment of the present invention.

FIG. 1 illustrates a four-way branch tube 10 as one embodiment of the tube assembly of the present invention. It will be understood that FIG. 1 is an enlarged view corresponding to a circled portion in the system of FIG. 4a. The four-way branch tube illustrated at 10 in FIG. 1 has four openings, that is, a first opening 11 to be connected to a puncture needle 24 for blood collection, a second opening 12 to be connected to a first blood bag 20, a third opening 13 to be connected to a second blood bag 21, and a fourth opening 14 having a plug 2 mounted thereon (see FIG. 4a). For brevity of description, a flow path communicating between the first and third openings 11 and 13 is designated a main flow path. With respect to the main flow path, the first opening 11 to be connected to the needle 24 is designated a proximal end and the second, third and fourth openings 12, 13 and 14 are designated distal ends.

Figure 2A:
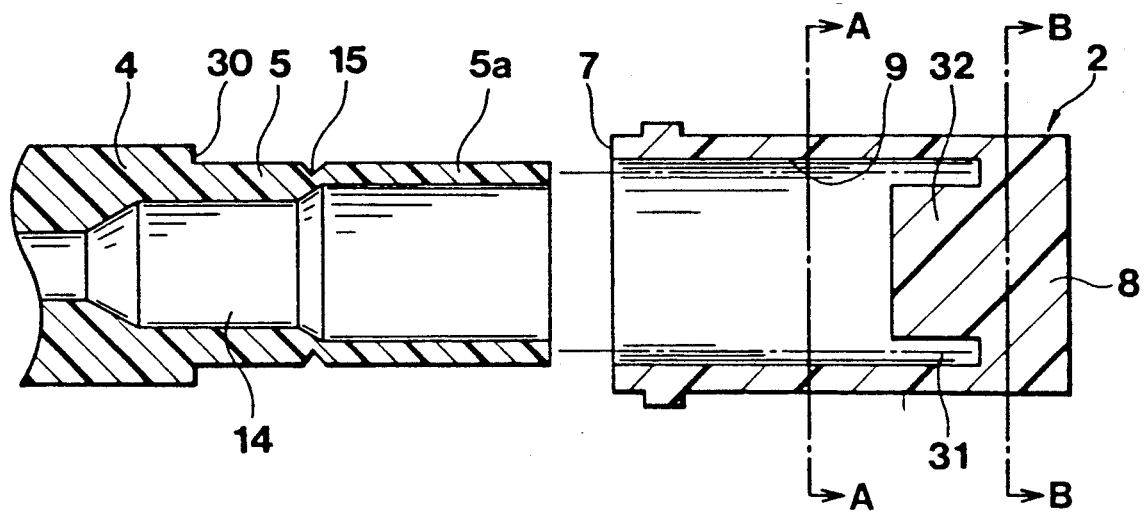
FIG. 2a is an exploded cross-sectional view of the tube assembly of the present invention showing a tube branch and a plug in a disassembled state.
Figure 2B:
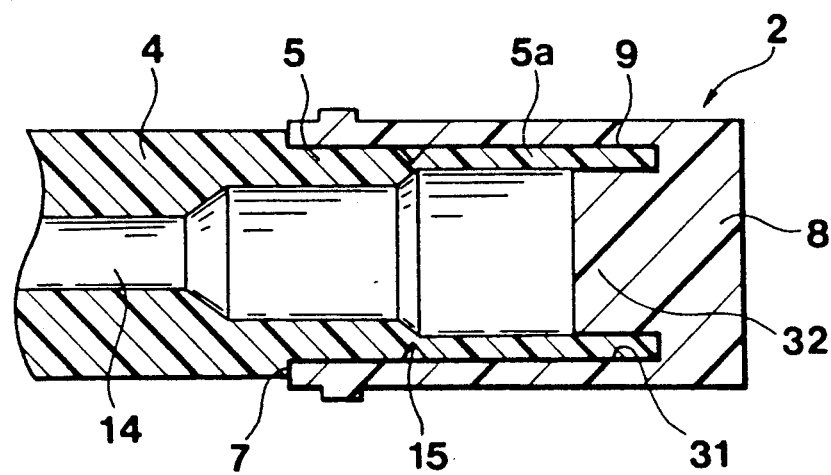
FIG. 2b is a cross-sectional view of the tube assembly showing the tube branch and the plug in an assembled state.

The feature of the present invention resides in a combination of the branch 4 having the fourth opening 14 and the plug 2 mounted on the branch 4. FIG. 2a is a cross-sectional view of the branch 4 and the plug 2 in an exploded state. A full assembly of these components is shown in FIG. 2b.

The branch 4 of the four-way branch tube having the fourth opening 14, which is considered a tubular body, includes an extension 5, sometimes referred to as an open end portion, having a reduced outer diameter as compared with the remaining of the branch for mounting the plug 2 thereon. The extension 5 thus forms a step 30 with the remaining branch on the outer wall.

The extension 5 is provided with a substantially annular frangible portion 15 at a predetermined position on its outer surface. The frangible portion 15 is between a proximal portion and a distal portion 5a of the extension 5 and enables breaking-away of the distal portion 5a. The term "substantially annular" means that the frangible portion may be an annular notch making a complete turn around the outer wall of the extension 5 or a series of disconnected notches circumferentially arranged on the outer wall of the extension 5 as long as the distal portion 5a can be readily broken away from the proximal portion of the extension 5 and hence, the tubular body.

The plug 2 is a generally tubular member including a wall portion having an open end 7 at one end and a grip portion having a closed end 8 at the other end. The wall portion of the plug 2 provides an inner wall 9 which extends from the open end 7 toward the closed end 8 and is adapted to be in sealing fit over the extension 5 of the branch. The inner wall 9 has substantially the same inner diameter as the outer diameter of the extension 5.

The grip portion of the plug 2 near the closed end 8 is substantially solid and includes a mesa portion 32 on a base. The annular channel 31 defines with the inner diameter of the inner wall 9 and the outer diameter of the the mesa portion 32 having substantially the inner diameter of the distal end 5a. The channel 31 is adapted to receive the distal end 5a of the extension 5.

Figure 3A:
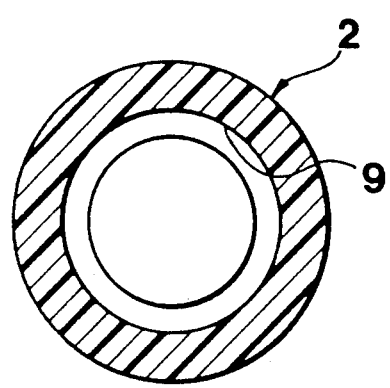
FIGS. 3a and 3b are cross-sectional views of the plug taken along lines A—A and B—B in FIG. 2a, respectively.
Figure 3B:
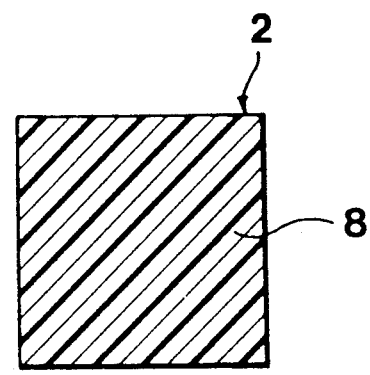

The grip portion of the plug 2 near the closed end 8 preferably has a cross-sectional shape other than a true circle. FIGS. 3a and 3b are the cross sections taken along lines A—A and B—B in FIG. 2a. The wall portion of the plug 2 adapted to fit over the extension 5 of the branch 4 has a substantially true circular cross section which is concentric with the extension 5 as shown in FIG. 3a. On the other hand, the grip portion of the plug 2 near the closed end 8 has a non-circular cross section. In the embodiment illustrated in FIG. 3b, the grip portion of the plug 2 has a square cross section. The grip portion of the plug 2 may be of any desired non-circular cross-section including rectangular and ellipsoidal shapes as long as it is easy to grasp.

Reference is now made to FIG. 2b where the plug 2 is mounted on the branch 4 defining the fourth opening to complete a tube assembly. In the assembled state, the distal portion 5a of the extension 5 of the branch is received in the channel 31, and the extension 5 is received in the wall portion of the plug 2 in a sealing engagement with the inner wall surface. The step 30 abuts the open end 7 of the plug 2 when the plug 2 is fully fitted over the extension 5 of the branch.

The plug 2 must be fitted over the extension 5 of the branch 4 in close sealing contact so the plug 2 may fully protect the extension 5 against an external stress, and no sliding motion occurs between the plug 2 and the extension 5 when the plug is grasped and twisted to tear off the distal portion 5a at the frangible portion 15. Engagement of the plug 2 over the extension 5 in a sealing fit prevents the flow path of the branch, that is, tubular body from being contaminated before breakage of the extension and removal of the plug.

The fourth opening 14 is closed by the plug 2 mounted on the extension 5 when the associated flow path is not used. When it is desired to connect another tubular member to the fourth opening 14, the distal portion 5a is twisted or broken away at the frangible portion 15 by grasping and turning the plug 2. Then the fourth opening 14 is ready for fluid communication with the other tubular member.

The engagement between the extension 5 of the tubular body and the plug 2 is not particularly limited as long as the engagement forms a seal and allows the distal portion 5a to be twisted off without any sliding motion between the extension 5 and the plug 2.

In general, medical tubings are made of polycarbonate and flexible vinyl chloride resin. When a plug is secured to such a tube, it is desired not to use an adhesive at the connection between the plug and the tube in order to avoid contamination to fluid being passed therethrough, typically blood. If a tube and a plug are made of compatible types of material, a blocking bond can be achieved between them by utilizing the heat applied for autoclave sterilization.

According to the present invention, the plug is formed of relatively flexible material such as polyvinyl chloride resin whereas the tubular body 1 having the frangible portion 15 is formed of rigid resin such as polycarbonate. The polycarbonate is susceptible to brittle fracture under an abrupt external stress, the tubular body formed thereof can be readily broken away or twisted off at the frangible portion 15. Although the plug 2 is formed of flexible resin such as polyvinyl chloride, the plug 2 itself has no frangible portion as opposed to the prior art plugs, and thus undergoes no troublesome distortion or deformation upon twisting.

According to the present invention, the tubular body 1 and the plug 2 are formed of rigid resin and flexible resin, respectively. The rigid and flexible resins used are not limited to the above-illustrated examples.

According to the present invention, the frangible portion is provided in the tubular body 1 of rigid resin such as polycarbonate, ensuring easy breakage at the frangible portion. The structure is relatively simple and the number of manufacturing steps is reduced.

Operation

The operation of the four-way branch tube having a plug 2 mounted on one branch as shown in FIG. 1 is described by referring to a system for plasmapheresis therapy having the branch tube incorporated therein.

Figure 4A:
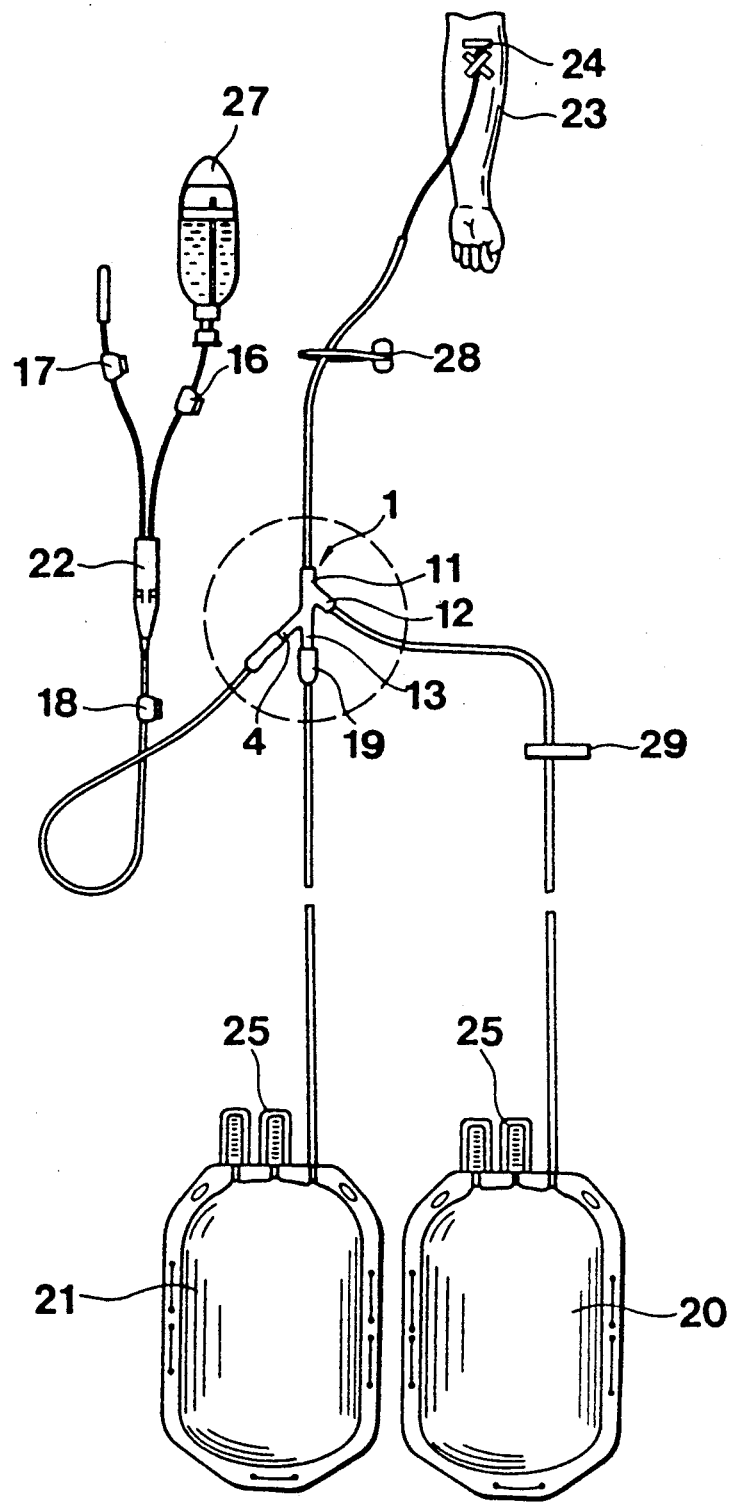
FIGS. 4a and 4b illustrate a plasmapheresis system having the tube assembly of the invention incorporated therein.

As shown in FIG. 4a, while clamps 16, 17 and 18 on the lines associated with the Y set 22 are closed, a needle connected to the line with clamp 16 is punctured into the saline bottle 27. Then the clamp 16 is opened and the clamp 18 is released to fill the Y set with saline. The clamp 18 is again closed.

During this operation, the extension 5 of the branch 4 of the four-way branch tube is kept normal or unbroken and engaged with the plug 2. The first opening 11 of the branch tube 10 is in fluid communication with the needle 24, and the second opening 12 in fluid communication with the first blood bag 20. The third opening 13 is connected to the second blood bag 21 although the click tip 19 is also kept normal or unbroken so that the flow path to the second blood bag 21 is closed.

The next step is to connect a connector at the free end of the Y set trunk 22 to the tubular body 1. The hemostat 29 is fastened on the second section of tubing connected to the first blood bag 20 in order to prevent reverse flow of medical liquid in the first blood bag 20.

Then the plug 2 is manually grasped and twisted to break the extension 5 at the frangible portion 15, removing the distal portion 5a to open the associated branch 4.

If a prior art plug with a frangible portion is manually twisted, the plug of flexible material tends to be easily deformed and is thus difficult to tear off in a click manner. In contrast, the plug 2 of flexible material is fitted over the tubular body of rigid resin such as polycarbonate having a frangible portion formed therein according to the present invention. When the plug 2 is gripped and twisted, the tubular body 1 snugly fitted in the plug 2 can be readily torn off at the frangible portion 15 without deformation even with a firm grip.

After the distal portion 5a is torn off along with the plug 2 at the frangible portion 15 by manually twisting the plug 2, the open end of the branch extension 5 is exposed. Then the connector of the Y set 22 is connected to the open end of the branch extension 5. Since the open end of the branch extension 5 is protruding and visible at this point, connecting operation is very easy and accurate. Contamination is avoided because the connector can be attached to the open end without inadvertent contact with any probably contaminated portion.

The next step is to collect blood from the donor 23. The first section of tubing is fastened by the hemostat 28 at a location near the needle 24. The puncture needle is inserted into the vein of the donor 23. After entry of blood into the blood collecting tube is observed, the hemostats 28 and 29 are taken off to communicate an open continuous flow path to the first blood bag 20.

Since the flow path to the second blood bag 21 is closed by the click tip 19 at this point, blood flows under gravity from the needle 24 to the first blood bag 20. Blood collection is continued until the first blood bag 20 is filled with a predetermined volume of blood. Then the section of tubing to the first blood bag 20 is sealed with a tube sealer or a pair of aluminum rings (not shown) and cut therebetween to separate the first blood bag 20.

Figure 4B:
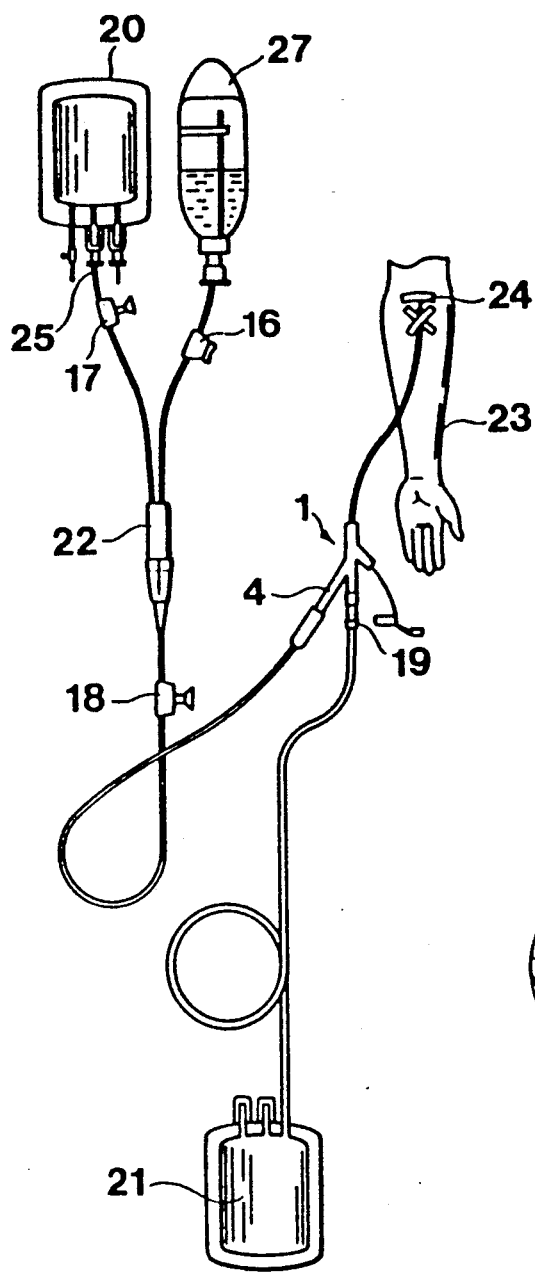
Figure 5:
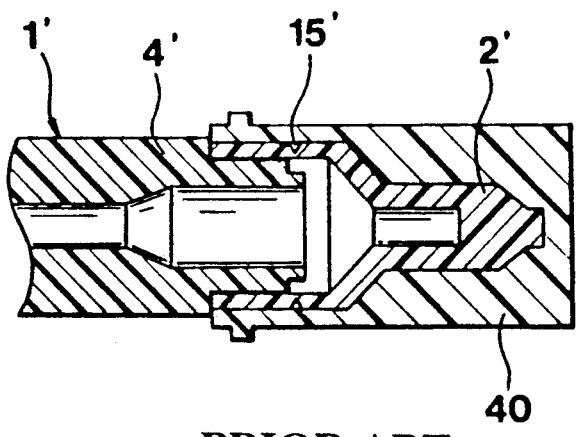
FIG. 5 is a cross-sectional view of a prior art tube assembly.

The whole blood in the first blood bag now removed is subjected to centrifugal separation. During the step, saline is transfused dropwise from the bottle 27 to the donor 23 through the Y set 22, the branch 4 with the plug removed, and the needle 24 as shown in FIG. 4b.

The platelet and red cell concentrates thus separated are independently return transfused to the donor 23. More particularly, an outlet 25 of the first blood bag 20 is connected to the second inlet tube of the Y set 22 having the clamp 17. Then the concentrates are returned to the donor 23 through the Y set 22, the four-way branch tube 10, and the needle 24.

At the end of return transfusion, the branch tube 1 is held in one hand, and the click tip 19 is manually torn off to open the flow path to the second blood bag 21. Blood is again collected from the donor 23 to the second blood bag 21 through the needle 24 which has been placed in the vein of the donor. Likewise the first blood bag 20, the blood collected in the second blood bag 21 is centrifugally separated and transfused back to the donor.

Industrial Applicability

The tube assembly of the present invention which includes a tubular body of rigid resin provided with a frangible portion and a plug means of flexible resin mounted in sealing fit on the tubular body has the following advantages.

(1) Since the plug means protects the open end portion of the tubular body against an external stress during manufacture and transportation, the open end portion is not fractured and the associated flow path is not contaminated until the time when the tubular body is used.

(2) The open end portion of the tubular body can be opened with the plug engaged thereon, eliminating the risk of contamination of the open end portion upon opening. This is particularly advantageous when the open end portion is used as a cell return inlet.

(3) The open end portion of the tubular body formed of rigid resin such as polycarbonate is provided with a frangible portion, and is opened by breaking at the frangible portion by bending or twisting. The frangible portion formed of rigid resin facilitates such breaking-away operation, eliminating the risk of deformation or distortion at the frangible portion as frequently occurred with the prior art structures.

(4) It suffices to engage and secure the plug over the open end portion of the tubular body, resulting in many benefits including a simplified structure, a reduced number of manufacturing steps, and a reduced manufacturing cost.

In the embodiment wherein the frangible portion is formed on the outer wall of the open end portion of the tubular body corresponding to the wall portion of the plug, after the open end portion of the tubular body is broken, the distal portion thereof can be removed along with the plug.

When the plug has a grip portion of non-circular cross section, it is convenient to manually grasp the plug to twist it.

We claim:

1. A breakaway tube assembly comprising:
   a tubular body formed of a rigid resin and having an open end;
   said tubular body including a substantially annular frangible portion at a predetermined position in proximity to said open end;
   said frangible portion fracturing upon application of a predetermined force thereto; and
   hollow plug means formed of a resin more flexible than said rigid resin forming said tubular body, said hollow plug means having first and second end portions, said first end portion being closed and second end portion being open;
   said hollow plug means being mounted over the outside of said tubular body to provide a seal for said open end of said tubular body, with said second end portion of said hollow plug means covering said substantially annular frangible portion of said tubular body; and
   said frangible portion of said tubular body fracturing before said seal breaks upon application of said predetermined force.

2. A breakaway tubular assembly according to claim 1, wherein said hollow plug means to bonded to said tubular body.

3. A breakaway tube assembly according to claim 1, wherein said frangible portion of said tubular body has a reduced outer diameter over which said hollow plug means is mounted.

4. A breakaway tubular assembly according to claim 3, wherein said seal is formed by bonding said closed first end portion of said hollow plug means to said tubular body.

5. A breakaway tube assembly according to claim 1, wherein said first end of said hollow plug means includes an annular groove which is dimensioned to receive and hold said annular frangible portion of said tubular body.

6. A breakaway tube assembly according to claim 1, wherein said hollow plug means includes a grip portion for applying a force to said hollow plug means which is sufficient to fracture said annular frangible portion of said tubular body.

* * * * *